United States Patent [19]
Stack

[11] Patent Number: 5,869,490
[45] Date of Patent: Feb. 9, 1999

[54] AZAHETEROCYCLYMETHYL DERIVATIVES OF 2,3,8,9-TETRAHYDRO-7H-1,4-DIOXINO (2,3-E) INDOL-8-ONE

[75] Inventor: Gary Paul Stack, Ambler, Pa.

[73] Assignee: American Home Products Corporation, Madison, N.J.

[21] Appl. No.: 947,565

[22] Filed: Oct. 9, 1997

Related U.S. Application Data

[60] Provisional application No. 60/28,409, Oct. 15, 1996.
[51] Int. Cl.$^6$ .................. A01N 43/60; C07D 405/00; C07D 401/00; C07D 319/02
[52] U.S. Cl. .................. 514/255; 514/338; 514/339; 514/454; 544/378; 546/276.7; 549/359
[58] Field of Search .................. 544/378; 546/276.7; 549/359; 514/255, 338, 339, 454

[56] References Cited

U.S. PATENT DOCUMENTS

| | | | |
|---|---|---|---|
| 5,318,988 | 6/1994 | Schohe-Loop et al. | 514/458 |
| 5,371,094 | 12/1994 | Heine et al. | 514/323 |

FOREIGN PATENT DOCUMENTS

WO9113872  9/1991  WIPO.

*Primary Examiner*—Mukund J. Shah
*Assistant Examiner*—Tamthom T. Ngo
*Attorney, Agent, or Firm*—Rebecca R. Barrett

[57] ABSTRACT

The compounds of formula I:

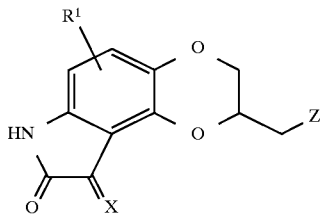

wherein
  X is $H_2$ or O;
  $R^1$ is hydrogen, hydroxy, halo, trifluoromethyl, trifluoromethoxy, alkyl, alkoxy, aralkoxy, alkanoyloxy, amino, mono- or di-alkylamino, alkanamido or alkanesulfonamido;
  Z is defined by

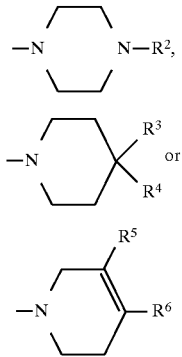

wherein
  $R^2$, $R^3$, $R^4$, $R^5$ and $R^6$ are as defined in the specification; or a pharmaceutically acceptable salt thereof, are useful for the treatment of brain dopamine dysregulation.

16 Claims, No Drawings

AZAHETEROCYCLYMETHYL DERIVATIVES OF 2,3,8,9-TETRAHYDRO-7H-1,4-DIOXINO (2,3-E) INDOL-8-ONE

BACKGROUND OF THE INVENTION

This application claims the benefit of U.S. Provisional application No. 60/28,409, filed Oct. 15, 1996 and is a continuation-in-part of that prior application which is incorporated by reference herein in its entirety.

PCT Int. Appl. WO 91 13,872 discloses dioxino[2,3-e] indole derivatives of the formula I, in which $R^1$ is H, alkyl, $CO_2R^2$, $CONHR^2$, cyano, halo, CHO, etc.; $R^2$ is H, alkyl, $(CH_2)_mY$; Y is cycloalkyl or cycloalkenyl, (substituted) phenyl, pyridyl, naphthyl, indolyl; m is 0–6; A and B are O, $CH_2$, S; and X is defined by formulas a, b or c, in which $R^2$ and m are defined as above, $R^3$ is hydrogen, $-CO_2R^2$, $-CONHR^2$, $-CN$, $-NHR^2$, $-CHO$, $-((CH_2)_m-Ar$, $-NR^2Ar$ or 1-benzimidazol-2-one, and $R^4$ is hydrogen, $C_1-C_6$ alkyl, $C_2-C_8$ alkenyl, $C_2-C_8$ alkynyl, $-(CH_2)_m-$ $(C_3-C_8)$ cycloalkyl or cycloalkenyl, $-(CH_2)_m-Ar$, $-CO_2R^2$, $-CONHR^2$, $-CN$ or $-CHO$, as serotonergic and dopaminergic agents useful for the treatment of CNS and cardiovascular disorders.

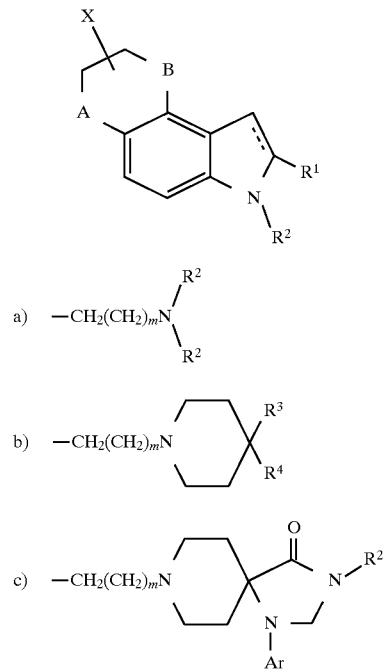

U.S. Pat. No. 5,318,988 discloses 2-aminomethyl-chromans of formula II as useful for treatment of diseases of the central nervous system. In this group of compounds, A, B and D are identical or different and represent hydrogen, halogen, cyano, azido, nitro, di- or tri-fluoromethyl, di- or tri-fluoromethoxy, hydroxyl or carboxyl, straight-chain or branched-chain alkyl, alkenyl, acyl, alkoxy or alkoxycarbonyl, or a mono- or di-substituted or unsubstituted amino, amido or sulfonamido, or A may be so defined and B and D taken together to form a 5 to 7-membered saturated, partly unsaturated, or aromatic carbocyclic ring or heterocyclic ring

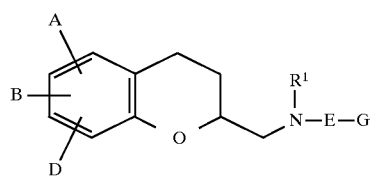

having up to two S, N or O atoms, optionally one or two carbonyl functions in the ring and optionally ring substituted by alkyl, branched alkyl or cycloalkyl; E represents a direct bond or represents straight chain or branched chain alkylene, alkenylene or alkynylene; G represents aryl having 6 to 10 carbon atoms or a 5 to 7-membered, saturated or unsaturated heterocyclic ring which is not bonded via N and has up to 3 hetero atoms from the series comprising N, O or S, to which a further saturated, partly unsaturated or aromatic 6-membered ring can optionally also be fused or cycloalkyl or a bridged bicarbocyclic ring. U.S. Pat. No. 5,371,094, related to the above, replaces $NR^1$-E-G in formula II with substituted piperidine, substituted tetrahypyridine or substituted dihydroisoindole and claims utility in the treatment of anxiety.

DESCRIPTION OF THE INVENTION

In accordance with this invention, there is provided a group of novel anti-psychotic agents of formula I:

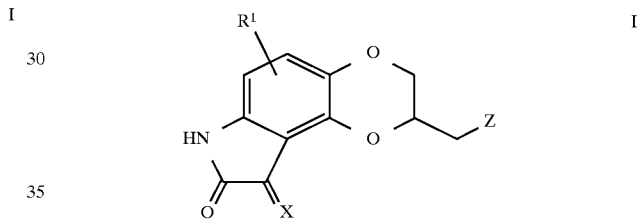

wherein
X is $H_2$ or O;
$R^1$ is hydrogen, hydroxy, halo, trifluoromethyl, trifluoromethoxy, alkyl of 1 to 6 carbon atoms, alkoxy of 1 to 6 carbon atoms, aralkoxy of 7 to 12 carbon atoms, alkanoyloxy of 2 to 6 carbon atoms, amino, mono- or di-alkylamino in which each alkyl group has 1 to 6 carbon atoms, alkanamido of 2 to 6 carbon atoms or alkanesulfonamido of 1 to 6 carbon atoms;
Z is

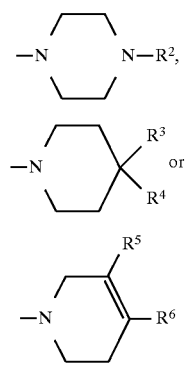

wherein
$R^2$ is hydrogen, alkyl of 1 to 6 carbon atoms, cycloalkyl of 3 to 8 carbon atoms, phenyl optionally substituted with $R^1$ as defined above; ω-phenylalkyl or ω-diphenylalkyl, in which the alkyl chain contains 1 to 4 carbon atoms and the phenyl is optionally substituted with $R^1$ as defined above, or $R^2$ is naphthyl, indolyl, indazolyl, thienyl, pyridinyl, pyrimidinyl, quinolinyl, benzoisothiazolyl or benzisoxazolyl, each optionally substituted with $R^1$ as defined above;

$R^3$ is hydrogen and $R^4$ is hydrogen, 1-benzimidazolyl-2-one, indolyl, benzoisothiazolyl or benzisoxazolyl, each optionally substituted with $R^1$ as defined above, or $R^4$ is —Y—Ar, in which Y is C=O, CHOH, or $(CH_2)_m$, wherein m is 0 to 4, and Ar is phenyl, optionally substituted with $R^1$ as defined above, or $R^3$ and $R^4$, taken together with the carbon atom to which they are attached form

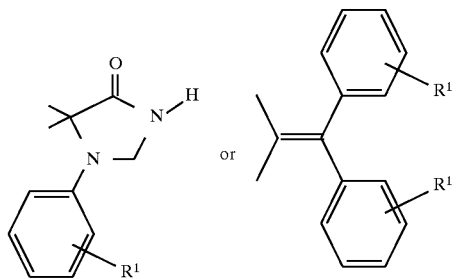

$R^5$ is hydrogen and $R^6$ is phenyl, naphthyl, thienyl, indolyl, benzoisothiazolyl or benzisoxazolyl, each optionally substituted with $R^1$ as defined above, or $R^5$ and $R^6$, taken together with the carbon atoms to which they are attached complete a benzene ring optionally substituted with $R^1$;

or a pharmaceutically acceptable salt thereof.

Of these compounds, the preferred members are those in which X and $R^1$ are defined as above, $R^2$ is phenyl, naphthyl, indolyl, indazolyl, thienyl, pyridinyl, pyrimidinyl, quinolinyl, benzoisothiazolyl or benzisoxazolyl, each optionally substituted with $R^1$ as defined above, $R^3$ is hydrogen and $R^4$ is 1-benzimidazolyl-2-one, indolyl, benzoisothiazolyl or benzisoxazolyl, each optionally substituted with $R^1$ as defined above, or $R^4$ is —Y—Ar, in which Y is C=O, and Ar is phenyl, optionally substituted with $R^1$ as defined above, $R^5$ is hydrogen and $R^6$ is phenyl, indolyl, benzoisothiazolyl or benzisoxazolyl, each optionally substituted with $R^1$ as defined above, or $R^5$ and $R^6$, taken together with the carbon atoms to which they are attached complete a benzene ring optionally substituted with $R^1$, defined above.

Most preferred are those members in which X is $H_2$ and $R^1$ is defined as above, $R^2$ is phenyl, indolyl, pyridinyl, pyrimidinyl, quinolinyl, benzoisothiazolyl or benzisoxazolyl, each optionally substituted with $R^1$ as defined above, $R^3$ is hydrogen and $R^4$ is 1-benzimidazolyl-2-one, indolyl, benzoisothiazolyl or benzisoxazolyl, each optionally substituted with $R^1$ as defined above, or $R^4$ is —Y—Ar, in which Y is C=O, and Ar is phenyl, optionally substituted with $R^1$ as defined above,. $R^5$ is hydrogen and $R^6$ is phenyl, optionally substituted with $R^1$ as defined above, or $R^5$ and $R^6$, taken together with the carbon atoms to which they are attached complete a benzene ring optionally substituted with $R^1$, as defined above. This invention relates to both the R and S stereoisomers of the aminomethyl-2,3,8,9-tetrahydro-7H-1,4-dioxino[2,3-e]indol-8-ones, as well as to mixtures of the R and S stereoisomers. Throughout this application, the name of the product of this invention, where the absolute configuration of the aminomethyl-2,3,8,9-tetrahydro-7H-1,4-dioxino[2,3-e]indol-8-ones is not indicated, is intended to embrace the individual R and S enantiomers as well as mixtures of the two.

The pharmaceutically acceptable salts are those derived from such organic and inorganic acids as: acetic, lactic, citric, tartaric, succinic, fumaric, maleic, malonic, mandelic, mallic, hydrochloric, hydrobromic, phosphoric, nitric, sulfuric, methanesulfonic, toluenesulfonic and similarly known acceptable acids.

The 2-azaheterocyclylmethyl-2,3,8,9-tetrahydro-7H-1,4-dioxino[2,3-e]indol-8-ones are prepared as illustrated below for examples in which Z is substituted piperazine. Specifically, the appropriately substituted nitroguaiacol is alkylated with allyl bromide in the presence of a suitable base such as sodium hydride and then

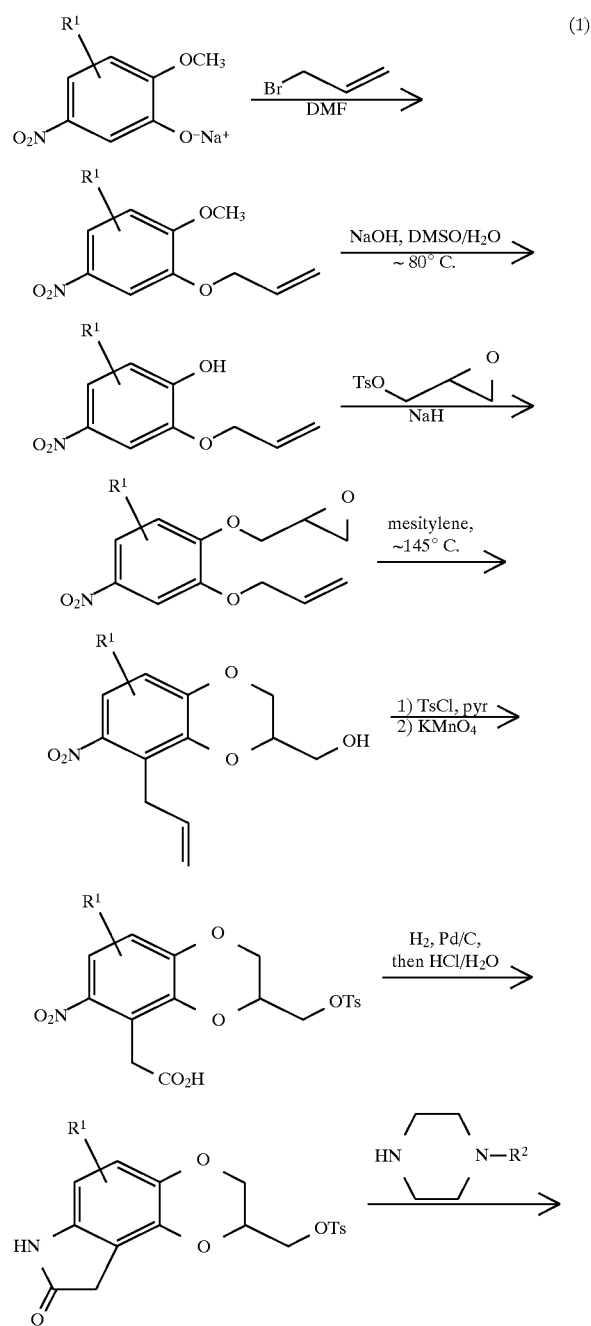

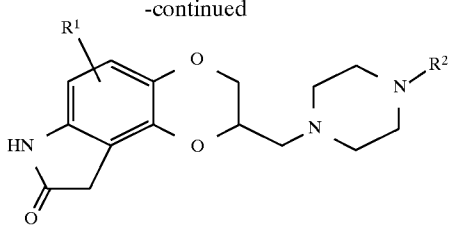

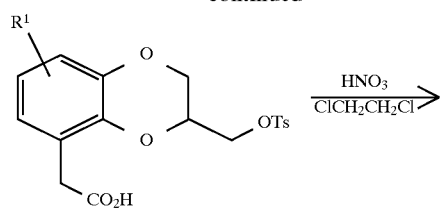

demethylated by a reagent such as sodium hydroxide. The resulting 4-nitro-2-allyloxyphenol is then alkylated with glycidyl tosylate or an epihalohydrin in the presence of a base such as sodium hydride and heated in a high boiling solvent such as mesitylene or xylene to effect both rearrangement of the allyl group and cyclization of the dioxan ring. The resulting primary alcohol is converted to the tosylate by reaction with p-toluenesulfonyl chloride in the presence of pyridine or alternatively to a halide by reaction with carbon tetrabromide or carbon tetrachloride in combination with triphenylphosphine. The allyl side chain is converted to an acetic acid moiety by oxidative cleavage with potassium permanganate and the nitro group is reduced to an amine with hydrogen and palladium on carbon and cyclized to the lactam with aqueous hydrochloric acid. Replacement of the tosylate or halide with the appropriately substituted azaheterocycle in some high boiling solvent such as dimethyl sulfoxide gives the title compounds of the invention.

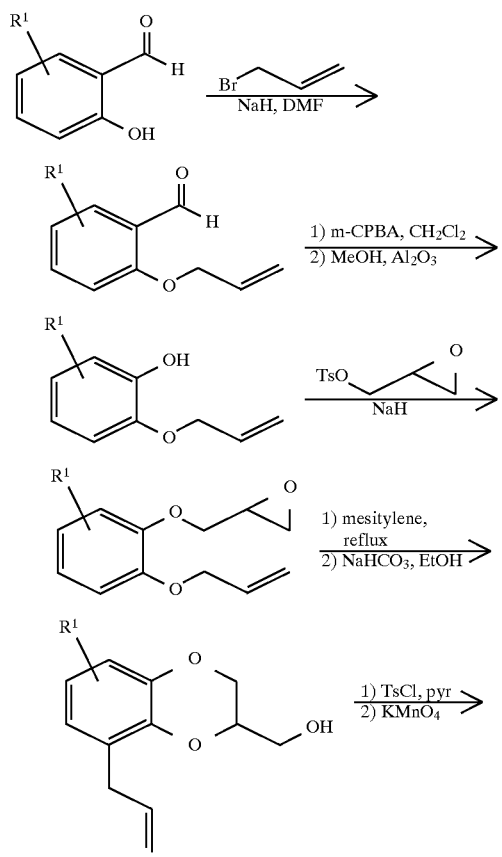

(1a)

The oxindoledioxan methyltosylate described in (1) may also be prepared as in (1a) above: the appropriately substituted salicylaldehyde is alkylated with allyl bromide in the presence of a suitable base such as sodium hydride. The aldehyde moiety is then converted to a phenol by treatment with m-chloroperoxybenzoic acid followed by cleavage of the intermediate formate ester with basic alumina in methanol. The resulting 2-allyloxyphenol is then alkylated with glycidyl tosylate or an epihalohydrin in the presence of a base such as sodium hydride and heated in a high boiling solvent such as mesitylene or xylene to effect rearrangement of the allyl group. Cyclization to the benzodioxanmethanol is completed by treatment with sodium bicarbonate in ethanol. Following conversion of the alcohol to a tosylate via p-toluenesulfonyl chloride in pyridine, the allyl side chain is oxidatively cleaved to an acetic acid moiety with potassium permanganate and the nitro group introduced by treatment with nitric acid in dichloroethane. Reduction of the nitro group and cyclization to the lactam are effected as in (1). A catalyst such as platinum oxide or platinum on sulfided carbon is preferred for the reduction when $R^1$ is a halogen.

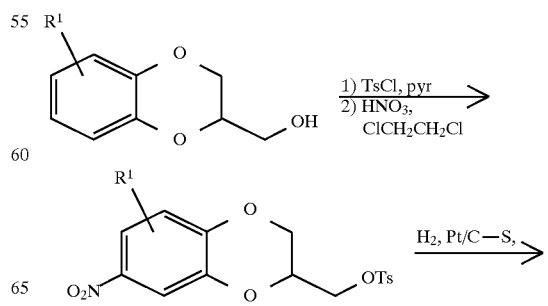

(1b)

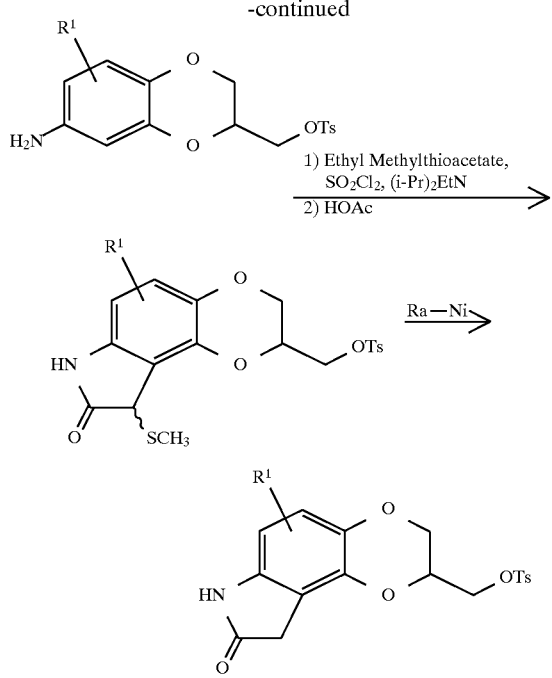

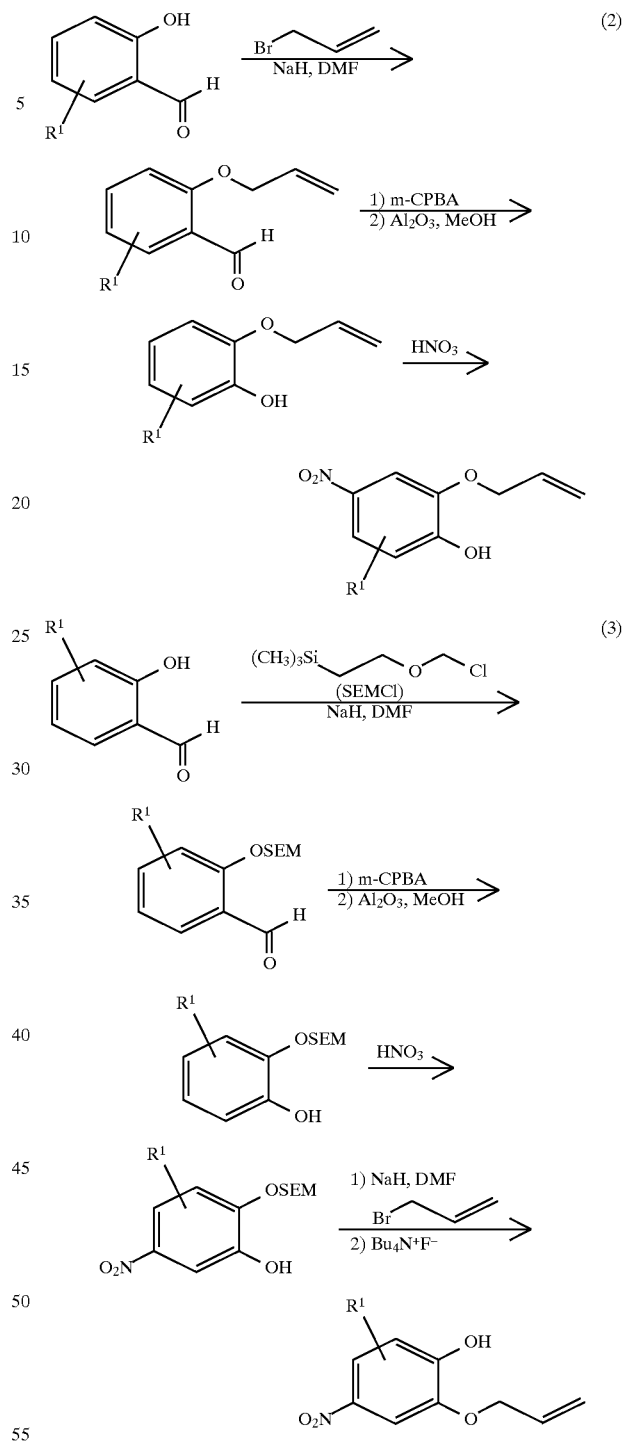

The oxindoledioxan methyltosylate may also be prepared from the appropriately substituted benzodioxan methanol as in (1b) above. Following conversion of the alcohol to the tosylate as described above, the nitro function is introduced by treatment with nitric acid in dichloroethane and reduced with hydrogen in the presence of a suitable catalyst such as platinum oxide or platinum on sulfided carbon. The oxindole is elaborated by a modification of the procedure of Gassman et. al. [*J. Amer. Chem. Soc.* 96, 5512 (1974)] and the resulting thiomethyl ether cleaved by treatment with Raney nickel.

Compounds of the invention in which X is oxygen (i.e., isatins) may be prepared by oxidation of the corresponding oxindoles. The appropriate nitroguaiacols are known compounds or may be prepared by one schooled in the art. Alternatively, the 4-nitro-2-allyloxyphenols utilized in process (1) described above may be prepared from the appropriately 5- or 6-substituted salicylaldehyde by procedure (2) below, or from the appropriately 3- or 4-substituted salicylaldehyde by procedure (3) below, in which [2-(trimethylsilyl)ethoxylmethyl chloride (SEMCl) is employed as a hydroxy protecting group during conversion of the aldehyde to the formate ester with meta-chloroperbenzoic acid followed by hydrolysis to the hydroxy group. The substituted azaheterocycles are known compounds or may be readily prepared by one schooled in the art. The compounds of the invention may be resolved into their enantiomers by conventional methods or, preferably, they may be prepared directly by substitution of (2R)-(−)-glycidyl 3-nitrobenzenesulfonate or tosylate (for the S benzodioxan methanamine) or (2S)-(+)-glycidyl 3-nitrobenzenesulfonate or tosylate (for the R enantiomer) in place of epihalohydrin or racemic glycidyl tosylate in the procedures above.

The compounds of this invention are dopamine autoreceptor agonists; that is, they serve to modulate the synthesis and release of the neurotransmitter dopamine. These compounds are also partial agonists at the postsynaptic dopamine $D_2$ receptor, capable of functioning as either agonists or antagonists depending on the level of dopaminergic stimulation. They thus serve to modulate dopaminergic neurotransmission and are thereby useful for treatment of disorders of the dopaminergic system, such as schizophrenia, schizoaffective disorder, Parkinson's disease, Tourette's syndrome and hyperprolactinemia and in the treatment of drug addiction such as the addiction to ethanol or cocaine and related illnesses.

The antipsychotic activity of the compounds of the invention was established by a determination of functional antagonism of dopamine receptors in vivo, specifically the compounds' ability to reduce mouse locomotor activity according to the method of Martin and Bendensky, J. Pharmacol. Exp. Therap. 229: 706–711, 1984, in which mice (male, CF-1, Charles River, 20–30 g) were injected with vehicle or various doses of each drug and locomotor activity was measured for 30 minutes using automated infrared activity monitors (Omnitech—8×8 inch open field) located in a darkened room. $ED_{50}$'s were calculated from the horizontal activity counts collected from 10 to 20 minutes after dosing using a nonlinear regression analysis with inverse prediction. When examined in this assay, the compounds of this invention produced $ED_{50}$'s of less than 5 mg/kg, sc.

Affinity for the dopamine D2 receptor was established by a modification of the standard experimental test procedure of Seemen and Schaus, European Journal of Pharmacology 203: 105–109, 1991, wherein homogenized rat striatal brain tissue is incubated with $^3$H-quinpirole and various concentrations of test compound, filtered and washed and counted in a Betaplate scintillation counter. The results of this testing with compounds representative of this invention are given below.

| Compound | $D_2$ Receptor Affinity ($IC_{50}$ (nM)) |
|---|---|
| Example 1 | 0.35 |
| Example 2 | 0.73 |
| Example 3 | 3.20 |
| Example 4 | 4.08 |
| Example 5 | 1.20 |
| Example 6 | 4.06 |
| Example 7 | 0.23 |

Hence, the compounds of this invention have potent affinity for dopamine receptors and produce a functional antagonism of dopamine receptors in vivo and thus are useful in the treatment of dopaminergic disorders such as schizophrenia, schizoaffective disorder, Parkinson's disease, Tourette's syndrome, hyperprolactinemia and drug addiction.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient. Based upon the activity profile and potency of the compounds of this invention compared to the clinically useful antipsychotic risperidone, it is considered that a starting dose of about 10 mg per day with gradual in crease in the daily dose to about 200 mg per day will provide the desired dosage level in the human.

The following examples illustrate the production of representative compounds of this invention.

INTERMEDIATE 1

3-Allyloxy-4-methoxynitrobenzene 97.5 g (0.51 mole) of the sodium salt of 5-nitroguaiacol was dissolved in one liter of DMF and 1.5 equivalents of allyl bromide added. The reaction was heated to 65° C. for two hours, after which time much of the dark color had discharged and tlc (1:1 $CH_2Cl_2$/hexane) indicated loss of starting material. The solvent was concentrated in vacuum and the residue washed with water. The product was isolated by filtration and dried in a vacuum. This gave 112 g of pale yellow solid. A sample recrystallized from methanol, gave m.p. 93°–94 ° C.

INTERMEDIATE 2

2-Allyloxy-4-nitrophenol

To one liter of dimethyl sulfoxide was added 750 ml of 2N aqueous sodium hydroxide and the mixture was heated to 65° C. The pale yellow solid 3-allyloxy-4-methoxynitrobenzene prepared above was added in portions over a 30 minute period and then the temperature was raised to 95° C. and maintained for 3 hours, after which time the starting material had been consumed. The mixture was allowed to cool and poured into a mixture of 1 L ice and 1 L 2N HCl. 73 Grams of crude but homogeneous (by tlc 1:1 $CH_2Cl_2$/hexane) desired product was isolated as a light brown solid by filtration. This material was subsequently dissolved in 1:1 hexane/methylene chloride and filtered through silica gel to give 68 g of pale yellow solid, which, when recrystallized from ethyl/acetate/hexane, gave m.p. 61°–62 ° C. The aqueous mother liquors from the initial crystallization above were extracted with 2 L of ethyl acetate. This was dried over sodium sulfate, filtered and evaporated to a dark oil. Column chromatography on silica with 1:1 $CH_2Cl_2$/hexane gave an additional 12 g of the title compound as a yellow solid. Elution with 2% MeOH in $CHCl_3$ gave 12 g of a dark oil which slowly crystallized in vacuum. This proved to be the Claisen product, 3-allyl-4-nitrocatechol.

INTERMEDIATE 3

2-(2-Allyloxy-4-nitrophenoxymethyl)-oxirane 20 g (0.50 mole) of 60% NaH/mineral oil was placed in a two liter flask and washed with 500 ml of hexane. 1 L of DMF was added, followed by 77 g (0.40 mole) of the 2-allyloxy-4-nitrophenol prepared in the previous step. Addition of the phenol was performed in portions under argon. After stirring the mixture for 30 minutes at room temperature under argon, 108 g (0.48 moles) of (R)-glycidyl tosylate was added and the mixture heated at 70°–75° C. under nitrogen overnight. Upon cooling, the DMF was removed in vacuum and replaced with one liter of methylene chloride. This was washed with 500 ml portions of 2N HCl, saturated sodium bicarbonate and saturated brine and dried over sodium sulfate. The mixture was filtered, concentrated to an oil in vacuum and column chromatographed on silica gel using 1:1 hexane/methylene chloride as eluant. This gave 43 g of product contaminated with traces of the two starting materials, followed by 21 g of pure product as a pale yellow solid. The impure material was recrystallized from 1.2 L of 10% ethyl acetate/hexane to give 34 g of pure (homogeneous on silica gel tlc with 1:1 hexane/methylene chloride) (R)-2-(2-allyloxy-4-nitrophenoxymethyl)-oxirane (m.p. 64° C).

Elemental Analysis for: $C_{12}H_{13}NO_5$

Calc'd: C, 57.37; H, 5.21; N, 5.58

Found: C, 57.50; H, 5.21; N, 5.43

INTERMEDIATE 4

(8-Allyl-7-nitro-2,3-dihydro-benzo(4)dioxin-2-yl)-methanol (R)-2-(2-Allyloxy-4-nitrophenoxymethyl)-oxirane (20 g, 80 mmoles) prepared as above was heated at 155° C. in mesitylene for 24 hours under nitrogen. Filtration of the black solid which formed gave 1.5 g of very polar material. Evaporation of the solvent in vacuum followed by column chromatography on silica gel with methylene chloride as eluant gave 10 g of recovered starting material and 7.5 g of the desired rearranged (S)-(8-allyl-7-nitro-2,3-dihydro-benzo(1,4)dioxin-2-yl)-methanol, which slowly crystallized on standing in vacuum (m.p. 67° C.). The yield based on recovered starting material is 75%.

Elemental Analysis for: $C_{12}H_{13}NO_5$

Calc'd: C, 57.37; H, 5.21; N, 5.58

Pound: C, 57.26; H, 5.20; N, 5.35

INTERMEDIATE 5

Toluene-4-sulfonic acid allyl-7-nitro-2.3-dihydro-benzo(1.4)dioxin-2-yl-methyl ester 9.55 g (38.0 mmole) of (S)-(8-allyl-7-nitro-2,3-dihydro-benzo(1,4)dioxin-2-yl)-methanol was dissolved in 465 ml of pyridine, 29.0 g (152 mmole) of p-toluenesulfonyl chloride was added and the mixture stirred at room temperature under nitrogen overnight. Water was then added to quench the excess tosyl chloride and the solvent was removed in vacuum and replaced with methylene chloride. This solution was washed with 2N HCl, with saturated sodium bicarbonate, and with saturated brine, and dried over magnesium sulfate. Filtration, evaporation in vacuum and column chromatography on silica gel with 1:1 hexane/methylene chloride as eluant gave 12.6 g (92%) of toluene-4-sulfonic acid (R)-allyl-7-nitro-2,3-benzo(1,4)dioxin-2-ylmethyl ester, which slowly crystallized to a tan solid (m.p. 60°–62° C.) upon standing.

Elemental Analysis for: $C_{19}H_{19}NO_7S$

Calc'd: C, 56.29; H, 4.72; N, 3.45

Found: C, 56.13; H, 4.58; N, 3.44

INTERMEDIATE 6

(6-Nitro-3-(toluene-4-sulfonyloxymethyl)-2,3-dihydro-benzo(1,4)dioxin-5-yl)-acetic acid Potassium permanganate (11.7 g, 0.074 mole) was placed in a flask which was equipped with a mechanical stirrer, a dropping funnel, and an ice bath. To this was added 150 ml of $H_2O$ and tetrabutylammonium chloride (1.0 g, 3.7 mmole) with stirring. The toluene-4-sulfonic acid (R)-allyl-7-nitro-2,3-benzo(1,4)dioxin-2-ylmethyl ester prepared above dissolved in 100 ml of benzene was slowly added through a dropping funnel and the reaction mixture was stirred further for 30 minutes in an ice bath. The ice bath was then removed and the mixture was stirred for 24 hours at room temperature. 30 g of sodium bisulfite was added to the mixture with good stirring in an ice bath and acidified with concentrated HCl until pH<3. The acidified clear yellow solution was then extracted with ethyl acetate and the combined extracts were dried over anhydrous magnesium sulfate. The concentrated residue was chromatographed on a silica gel column using ethyl acetate as an eluant to give 6.3 g (60%) of (R)-(6-nitro-3-(toluene-4-sulfonyloxymethyl)-2,3-dihydro-benzo(1,4)-dioxin-5-yl)-acetic acid as a pale yellow solid. Crystallization from methylene chloride gave a light yellow 'solid with m.p. 158°–159° C.

Elemental Analysis for: $C_{18}H_{17}NO_9S \cdot \frac{1}{4}H_2O$

Calc'd: C, 50.52; H, 4.12; N, 3.27

Found: C, 50.51; H, 3.83; N, 3.12

INTERMEDIATE 7

2-(Toluene-4-sulfonyloxymethyl)-2,3,8,9-tetrahydro-7H-1,4-dioxino[2,3-e]-indol-8-one The carboxylic acid (6.0 g, 0.0142 mole) obtained above was ground into a fine powder. To this was added 300 ml of water and 5 ml of 2.5N NaOH until the pH was 8, and the heterogeneous solution was stirred for 30 minutes until the solid was evenly dispersed. 1.0 g of 10% Pd on carbon was then added and the mixture was hydrogenated on a Parr shaker for 24 hours at 52 psi of hydrogen. The catalyst was filtered off and washed with water. The volume of the filtrate was then reduced by half and acidified with 15 ml of concentrated HCl while stirring in an ice bath to precipitate a white solid acid product, (R)-(6-amino-3-(toluene-4-sulfonyloxymethyl)-2,3-dihydro-benzo(1,4)dioxin-5-yl)-acetic acid. This heterogeneous solution was then heated at 50° C. for 24 hours. As time passed, tlc (5% methanol/$CH_2Cl_2$ on silica gel) showed that the amino acid was slowly replaced with lactam, and the reaction mixture became clear briefly and then the title compound started to precipitate as a white solid. After the mixture was cooled to room temperature and stirred for an additional hour, the white solid was filtered, washed with diethyl ether and dried in a vacuum at room temperature. The product (R)-2-(toluene-4-sulfonyloxymethyl)-2,3,8,9-tetrahydro-7H-1,4-dioxino[2,3-e]indol-8-one (m.p. 225°–227° C.) was pure without further recrystallization and weighed 4.2 g (79%).

Elemental Analysis for: $C_{18}H_{17}NO_6S$
Calc'd: C, 57.59; H, 4.57; N, 3.73
Found: C, 57.34; H, 4.55; N, 3.69

EXAMPLE 1

2-(3,4-Dihydro-1H-isoquinolin-2-ylmethyl)-2,3,8,9-tetrahydro-7H-1,4-dioxino[2,3-e]indol-8-one (R)-2-(Toluene-4-sulfonyloxymethyl)-2,3,8,9-tetrahydro-7H- 1,4-dioxino[2,3-e]indol-8-one (1.05 g, 2.80 mmole) and tetrahydroisoquinoline (1.60 ml, 12.6 mmole) were combined in 30 ml of dry DMSO and heated to 85° C. for 4.5 hours under a nitrogen atmosphere. The reaction was cooled and taken into 400 ml of 1:1 hexane/ethyl acetate. This was washed with 200 ml of water, with 200 ml of saturated brine, dried over $MgSO_4$, filtered and concentrated to yield an oil. This oil was column chromatographed on silica gel using 0.75% methanol/$CH_2Cl_2$ as eluant to give the free base of the title compound as a yellow oil (0.77 g, 82%). This oil was crystallized from ethanol with the addition of a solution of fumaric acid in hot ethanol to give 0.61 g of the (S) enantiomer of the title compound as a light yellow solid fumarate, m.p. 195°–196° C.

Elemental Analysis for: $C_{20}H_{20}N_2O_3 \cdot C_4H_4O_4$
Calc'd: C, 63.71; H, 5.35; N, 6.19
Found: C, 63.39; H, 5.39; N, 6.01

EXAMPLE 2

2-(4-(4-Fluoro-benzoyl)-piperidin-1-ylmethyl]-2,3,8,9-tetrahydro-7H-1,4-dioxino[2,3-e]indol-8-one (R)-2-(Toluene-4-sulfonyloxymethyl)-2,3,8,9-tetrahydro-7H- 1,4-dioxino[2,3-e]indol-8-one (1.03 g, 2.75 mmole), 4-(4-fluorobenzoyl)piperidine p-toluenesulfonate (4.68 g, 12.4 mmole) and diisopropylethylamine (2.15 ml, 12.3 mmole) were combined in 70 ml of dry DMSO and heated to 85° C. for 5 hours under a nitrogen atmosphere. The reaction was cooled and taken into 400 ml of 1:1 hexane/ethyl acetate. This was washed with 200 ml of water, with 200 ml of saturated brine, dried over $MgSO_4$, filtered and concentrated to yield an oil. This oil was column chromatographed on silica gel using 0.75% methanol/$CH_2Cl_2$ as eluant to give the free base of the title compound as a yellow oil (0.40 g, 40%). This oil was crystallized from ethanol with the addition of a solution of fumaric acid in hot ethanol to give 0.37 g of the (S) enantiomer of the title compound as a light yellow solid fumarate, m.p. 237°–238° C.

Elemental Analysis for: $C_{23}H_{23}FN_2O_4 \cdot C_4H_4O_4$
Calc'd: C, 61.59; H, 5.17; N, 5.32
Found: C, 61.41; H, 4.95; N, 5.30

EXAMPLE 3

2-(4-Oxo-1-phenyl-1,3,8-triaza-spiro[4,5]dec-8-ylmethyl)-2,3,8,9-tetrahydro-7H-1,4-dioxino-[2,3-e]indol-8-one (R)-2-(Toluene-4-sulfonyloxymethyl)-2,3,8,9-tetrahydro-7H- 1,4-dioxino[2,3-e]indol-8-one (1.04 g, 2.77 mmole) and 1-phenyl-1,3,8-triazaspirodecan-4-one (2.89 g, 12.5 mmole) were combined in 40 ml of dry DMSO and heated to 85° C. for 4 hours under a nitrogen atmosphere. The reaction was cooled and taken into 400 ml of 1:1 hexane/ethyl acetate. This was washed with 200 ml of water, with 200 ml of saturated brine, dried over $MgSO_4$, filtered and concentrated to yield an oil. This oil was column chromatographed on silica gel using 2.5% methanol/$CH_2Cl_2$ as eluant to give the free base of the title compound as a yellow oil (0.40 g, 33%). This oil was crystallized from ethanol with the addition of a solution of fumaric acid in hot ethanol to give 0.31 g of the (S) enantiomer of the title compound as a light yellow solid hemifumarate, hemihydrate, m.p. 264°–265.5° C.

Elemental Analysis for: $C_{24}H_{26}N_4O_4 \cdot 0.5\ C_4H_4O_4 \cdot 0.5\ H_2O$
Calc'd: C, 62.26; H, 5.83; N, 11.17
Found: C, 62.38; H, 5.75; N, 11.01

EXAMPLE 4

2-[4-(2-Oxo-2,3-dihydro-benzimidazol-1-yl)-piperidin-1-ylmethyl]-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (1.04 g, 2.77 mmole) and 4-(2-oxo-2,3-dihydro-benzimidazol-1-yl)-piperidine (2.71 g, 12.5 mmole) were combined in 40 ml of dry DMSO and heated to 85° C. for 4 hours under a nitrogen atmosphere. The reaction was cooled and taken into 400 ml of 1:1 hexane/ethyl acetate. This was washed with 200 ml of water, with 200 ml of saturated brine, dried over $MgSO_4$, filtered and concentrated to yield an oil. This oil was column chromatographed on silica gel using 1% methanol/$CH_2Cl_2$ as eluant to give the free base of the title compound as a yellow oil (0.65 g, 53%). This oil was crystallized from ethanol with the addition of a solution of fumaric acid in hot ethanol to give 0.61 g of the (S) enantiomer of the title compound as a light yellow solid fumarate, hemihydrate, m.p. 262°–263.5° C.

Elemental Analysis for: $C_{23}H_{24}N_4O_4 \cdot C_4H_4O_4 \cdot 0.5\ H_2O$
Calc'd: C, 59.44; H, 5.36; N, 10.27
Found: C, 56.11; H, 5.31; N, 10.24

EXAMPLE 5

2-(4-Phenyl-3,6-dihydro-2H-pyridin-1-ylmethyl)-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (1.04 g, 2.77 mmole), 4-phenyltetrahydropyridine hydrochloride (2.45 g, 12.5 mmole) and diisopropylethylamine (2.20 ml, 12.5 mmole) were combined in 50 ml of dry DMSO and heated to 85° C. for 5 hours under a nitrogen atmosphere. The reaction was cooled and taken into 400 ml of 1:1 hexane/ethyl acetate. This was washed with 200 ml of water, with 200 ml of saturated brine, dried over $MgSO_4$, filtered and concentrated to yield an oil. This oil was column chromatographed on silica gel using 1.5% methanol/$CH_2Cl_2$ as eluant to give 0.15 g of the (S) enantiomer of the free base of the title compound as a light yellow solid one-quarter hydrate, m.p. 264°–265° C.

Elemental Analysis for: $C_{22}H_{22}N_2O_3 \cdot 0.25\ H_2O$
Calc'd: C, 72.01; H, 6.18; N, 7.63
Found: C, 72.28; H, 6.08; N, 7.65

EXAMPLE 6

2-[4-(1H-Indol-4-yl)-piperazin-1-ylmethyl]-2,3,8,9-tetrahydro-7H-1.4-dioxino[2.3-e]indol-8-one (R)-2-(Toluene-4-sulfonyloxymethyl)-2,3,8,9-tetrahydro-7H-1,4-dioxino[2,3-e]indol-8-one (1.0 g, 2.7 mmole) and 4-(1H-indol-4-yl)-piperazine (2.0 g, 10 mmole) were combined in 30 ml of dry DMSO and heated to 80° C. for 4 hours under an argon atmosphere. After cooling to room temperature, the mixture was diluted with 400 ml of 1:1 ethyl acetate/hexane and washed with 400 ml of saturated sodium bicarbonate solution, with two 250 ml portions of water and with saturated brine. The mixture was dried over sodium sulfate, filtered and concentrated in vacuum to yield an oil, which was column chromatographed on silica gel using 0.5% methanol/CHCl$_3$ as eluant. The free base of the title compound (0.80 g) thus obtained was crystallized from methanol with the addition of one equivalent of fumaric acid to give 077 g of the (S) enantiomer of the title compound as a white solid fumarate, m.p. 237°–238° C.

Elemental Analysis for: $C_{23}H_{24}N_4O_3 \cdot C_4H_4O_4$
Calc'd: C, 62.30; H, 5.42; N, 10.76
Found: C, 62.02; H, 5.38; N, 10.70

INTERMEDIATE 8

(R)-2-Toluene-4-sulfonyloxymethyl)-6-fluoro-2,3-dihydrobenzo[1,4]dioxin (S)-(6-fluoro-2,3-dihydrobenzo(1,4 dioxin-2-yl)-methanol (17 g, 92 mmole) was dissolved in one liter of pyridine. To this solution was added 38 g (0.20 mole) of p-toluenesulfonyl chloride and the mixture stirred at room temperature under nitrogen for three days. The reaction was cooled in an ice-water bath and to it was added slowly 10 ml of water. The mixture was stirred at room temperature for 2 hours and then the solvent was removed under vacuum and replaced with 800 ml of methylene chloride. This solution was washed twice with 500 ml of 1N HCl (aq), with saturated aqueous sodium bicarbonate, and with saturated brine and dried over sodium sulfate. Filtration, evaporation in vacuum and column chromatography on silica gel with 50% hexane in dichloromethane as eluent gave 25.1 g (89%) of the title compound as an off-white solid. $^1$H (CDCl$_3$) doublet, 7.86 δ (2 H); doublet, 7.32 δ (2 H); doublet of doublets, 6.65 δ (1 H); multiplet, 6.58 δ (2 H); multiplet, 4.34 δ (1 H); multiplet, 4.20 δ (3 H); multiplet, 4.00 δ (1 H); singlet, 2.43 δ (3 H).

INTERMEDIATE 9

(R)-2-Toluene-4-sulfonyloxymethyl)-6-fluoro-7-nitro-2,3-dihydrobenzo[1,4]dioxin (R)-2-Toluene-4-sulfonyloxymethyl)-6-fluoro-2,3-dihydrobenzo[1,4]dioxin (25.1 g, 74 mmole) was dissolved in 250 ml of dichloroethane and cooled to 0° C. in an ice/water bath. To this cooled solution was added dropwise over a 15 minute period a solution of nitric acid (sp. gr. 1.49) in 60 ml of dichloroethane. The mixture was stirred at 0° C. under nitrogen for two hours, after which time the reaction was quenched by the addition of 500 g of ice. The mixture was diluted to 700 ml with methylene chloride and washed with saturated aqueous sodium bicarbonate solution, with water, with saturated brine and dried over sodium sulfate. Filtration and evaporation in vacuum gave 25 g of crude product. This was column chromatographed on silica gel using 1:1 hexane/ethyl acetate as eluant to give 21 g of the title compound as a yellow solid. $^1$H (CDCl$_3$) doublet, 7.80 δ (2 H); doublet, 7.50 δ (1 H); doublet, 7.38 δ (2 H); doublet, 6.76 δ (1 H); multiplet, 4.40 δ (2 H); multiplet, 4.25 δ (2 H); multiplet, 4.15 δ (1 H); singlet, 2.43 δ (3 H).

INTERMEDIATE 10

(R)-2-Toluene-4-sulfonyloxymethyl)-6-fluoro-7-amino-2,3-dihydrobenzo[1,4]dioxin (R)-2-Toluene-4-sulfonyloxymethyl)-6-fluoro-7-nitro-2,3-dihydrobenzo[1,4]dioxin (21 g, 55 mmole) was added to a suspension of 2.0 g of 10% palladium on carbon in 250 ml of methanol. To this was added 15 ml of 4N isopropanolic HCl. The mixture was hydrogenated for 20 hours using a Parr apparatus at 50–60 psi of hydrogen. The mixture was then filtered through celite and the catalyst washed with additional methanol. The filtrate was concentrated in vacuum to give 21.4 g of the title compound as a gray solid hydrochloride. $^1$H (DMSO-d$_6$) doublet, 7.80 δ (2 H); doublet, 7.47 δ (2 H); doublet, 6.95 δ (1 H); doublet, 6.85 δ (1 H); multiplet, 4.40 δ (1 H); multiplet, 4.25 δ (3 H); multiplet, 4.00 δ (1 H); singlet, 2.40 δ (3 H).

INTERMEDIATE 11

(R)-2-(Toluene-4-sulfonyloxymethyl)-6-fluoro-2,3,8,9-tetrahydro-7H-1,4-dioxino[2,3-e]indol-8-one In a three-neck flask equipped with a dropping funnel, thermometer and a nitrogen inlet was placed 6.15 ml (48.0 mmole) of ethyl methylthioacetate and 65 ml of dry methylene chloride. The solution was cooled to −78° C. by means of a dry ice/isopropanol bath and to it was added dropwise over a 5 minute period a solution of 3.80 g (47.0 mmole) of sulfuryl chloride in 30 ml of methylene chloride. The reaction was maintained at −78° C. for 30 minutes. To the mixture was added dropwise over a one hour period a solution of (R)-2-toluene-4-sulfonyloxymethyl)-6-fluoro-7-amino-2,3-dihydrobenzo[1,4]dioxin (15.7 g, 45.0 mmole) and Proton Sponge (11.7 g, 47.0 mmole) in 150 ml of methylene chloride. The mixture was stirred a −78° C. for two hours, then 9.5 g (54 mmole) of diisopropylethylamine in 20 ml of dichloromethane added dropwise over 10 minutes and stirring continued for an additional hour at −78° C., after which the reaction was allowed to come to room temperature and stirred for 8 hours under nitrogen. The resulting solution was diluted to 500 ml with methylene chloride and washed with saturated brine, dried over magnesium sulfate, filtered and concentrated in vacuum to a brown oil. This was dissolved in 200 ml of glacial acetic acid and stirred for 10 hours at room temperature under a nitrogen atmosphere. The solvent was then removed in vacuum and replaced with 500 ml of methylene chloride. The mixture was washed with 300 ml of saturated aqueous sodium bicarbonate and 300 ml saturated brine, dried over magnesium sulfate, filtered and concentrated in vacuum to a brown oil, which was column chromatographed on silica gel using 2% methanol in methylene chloride as eluant. The light brown solid (13.0 g, 66%) thus obtained was dissolved in 200 ml of tetrahydrofuran (THF) and added to a suspension in 600 ml of THF of approximately 200 g of Raney nickel (Ra—Ni weighed as a slurry in water), which had been washed with water, with 0.5% aqueous acetic acid, again with water and finally with THF. The reaction was stirred at room temperature for 8 hours, then the solution decanted and the catalyst washed thoroughly with THF. The combined organic fractions were concentrated in vacuum and the product column chromatographed on silica gel using methylene chloride as eluant. The title compound (4.54 g, 40%) was isolated as an off-white solid, m.p. 205°–206° C.

Elemental Analysis for: $C_{18}H_{16}FNO_6S \cdot 0.25 H_2O$
Calc'd: C, 54.34; H, 4.18; N, 3.52
Found: C, 54.12; H, 4.24; N, 3.41

EXAMPLE 7

2-(3,4-Dihydro-1H-isoguinolin-2-ylmethyl)-6-fluoro-2,3,8,9-tetrahydro-7H-1,4-dioxino[2,3-e]indol-8-one (R)-2-(Toluene-4-sulfonyloxymethyl)-6-fluoro-2,3,8,9-tetrahydro-7H-1,4-dioxino[2,3-e]indol-8-one (1.0 g, 2.5 mmole) and tetrahydroisoquinoline (1.3 g, 10 mmole) were combined in 30 ml of dry DMSO and heated at 80°–90° C. for 4 hours under an argon atmosphere. After cooling to room temperature, the mixture was diluted with 500 ml of 1:1 ethyl acetate/hexane and washed with 250 ml of saturated aqueous sodium bicarbonate and with two 250 ml portions of water, dried over sodium sulfate, filtered and concentrated in vacuum. The residue was column chromatographed on silica gel using 0.5% methanol/CHCl$_3$ as eluant to give the free base of the title compound as a pale yellow oil. This was crystallized from ethanol with the addition of one equivalent of fumaric acid to give 0.79 g of the (S) enantiomer of the title compound as a pale orange solid fumarate, m.p. 219°–220° C.

Elemental Analysis for: $C_{20}H_{19}FN_2O_3 \cdot C_4H_4O_4$

Calc'd: C, 61.27; H, 4.93; N, 5.95

Found: C, 61.12; H, 4.84; N, 5.83

EXAMPLE 8

2-[4-(1H-Indol-3-yl)-1-piperidinylmethyl]-6-fluoro-2,3,8,9-tetrahydro-7H-1,4-dioxino[2,3-e]indol-8-one (R)-2-(Toluene-4-sulfonyloxymethyl)-6-fluoro-2,3,8,9-tetrahydro-7H-1,4-dioxino[2,3-e]indol-8-one (1.0 g, 2.5 mmole) and 4-(1H-indol-3-yl)piperidine (2.0 g, 10 mmole) are combined in 30 ml of dry DMSO and heated at 80°–90° C. for 4 hours under an argon atmosphere. After cooling to room temperature, the mixture is diluted with 500 ml of 1:1 ethyl acetate/hexane and washed with 250 ml of saturated aqueous sodium bicarbonate and with two 250 ml portions of water, dried over sodium sulfate, filtered and concentrated in vacuum. The residue is column chromatographed on silica gel using 0.5% methanol/CHCl$_3$ as eluant to give the free base of the title compound. The product is crystallized from ethanol with the addition of one equivalent of fumaric acid to give the (S) enantiomer of the title compound as a fumarate salt.

EXAMPLE 9

2-[4-(1,2-Benzisothiazol-3-yl)-1-piperazinylmethyl]-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (1.0 g, 2.7 mmole) and 1-(1,2-benzisothiazol-3-yl)piperazine (2.2 g, 10 mmole) are combined in 30 ml of dry DMSO and heated at 80°–90° C. for 4 hours under an argon atmosphere. After cooling to room temperature, the mixture is diluted with 500 ml of 1:1 ethyl acetate/hexane and washed with 250 ml of saturated aqueous sodium bicarbonate and with two 250 ml portions of water, dried over sodium sulfate, filtered and concentrated in vacuum. The residue is column chromatographed on silica gel using 0.5% methanol/CHCl$_3$ as eluant to give the free base of the title compound. The product is crystallized from ethanol with the addition of one equivalent of fumaric acid to give the (S) enantiomer of the title compound as a fumarate salt.

EXAMPLE 10

2-[4-(6-Fluoro-1,2-benzisoxazol-3-yl)-1-piperidinylmethyl]-2,3,8,9-tetrahydro-7H-1,4-dioxino[2,3-e]indol-8-one (R)-2-(Toluene-4-sulfonyloxymethyl)-2,3,8,9-tetrahydro-7H-1,4-dioxino[2,3-e]indol-8-one (1.0 g, 2.7 mmole) and 4-(6-fluoro-1,2-benzisoxazol-3-yl)-1-piperidine (2.2 g, 10 mmole) are combined in 30 ml of dry DMSO and heated at 80°–90° C. for 4 hours under an argon atmosphere. After cooling to room temperature, the mixture is diluted with 500 ml of 1:1 ethyl acetate/hexane and washed with 250 ml of saturated aqueous sodium bicarbonate and with two 250 ml portions of water, dried over sodium sulfate, filtered and concentrated in vacuum. The residue is column chromatographed on silica gel using 0.5% methanol/CHCl$_3$ as eluant to give the free base of the title compound. The product is crystallized from ethanol with the addition of one equivalent of fumaric acid to give the (S) enantiomer of the title compound as a fumarate salt.

EXAMPLE 11

4-Fluoro-8-[4-(1H-indol-3-yl)-3,6-dihydro-2H-pyridin-1-ylmethyl]-1,3,7,8-tetrahydro-6,9-dioxa-3-aza-cyclopenta[a]naphthalen-2-one (R)-2-(Toluene-4-sulfonyloxymethyl)-6-fluoro-2,3,8,9-tetrahydro-7H-1,4-dioxino[2,3-e]indol-8-one (0.92 g, 2.34 mmole) 4-(1H-indol-3-yl)-3,6-dihydro-2H-pyridine (1.30 g, 6.6 mmole) were combined in 40 ml of dry. DMSO and heated at 80° C. for 5 hours under a nitrogen atmosphere. After cooling to room temperature, the mixture was diluted with 150 ml of water and extracted with 0.4% methanol in ethyl acetate. The organic extract was washed with 100 ml of saturated aqueous sodium bicarbonate solution, dried over magnesium sulfate, filtered and concentrated to a red oil in vacuum. The residue was column chromatographed on silica gel using first 10% dichloromethane/hexane, then dichloromethane and finally 2% methanol in dichloromethane to give the desired product as an oil contaminated with DMSO. The oil was redissolved in ethyl acetate and washed three times with 150 ml portions of water, dried over magnesium sulfate, filtered and concentrated to a yellow oil in vacuum. Addition of ethanol to the oil gave 0.25 g of the (S) enantiomer of the title compound as a yellow solid, m.p. 230° C.

Elemental Analysis for: $C_{24}H_{22}FN_3O_3 \cdot 0.5\ H_2O$

Calc'd: C, 67.28; H, 5.41; N, 9.81

Found: C, 67.18; H, 5.34; N, 9.86

What is claimed is:

1. A compound of formula I

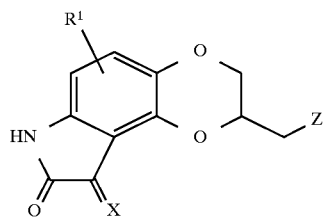

wherein

X is H$_2$ or O;

R$^1$ is hydrogen, hydroxy, halo, trifluoromethyl, trifluoromethoxy, alkyl of 1 to 6 carbon atoms, alkoxy of 1 to 6 carbon atoms, aralkoxy of 7 to 12 carbon atoms, alkanoyloxy of 2 to 6 carbon atoms, amino, mono- or di-alkylamino in which each alkyl group has 1 to 6 carbon atoms, alkanamido of 2 to 6 carbon atoms or alkanesulfonamido of 1 to 6 carbon atoms;

Z is defined by

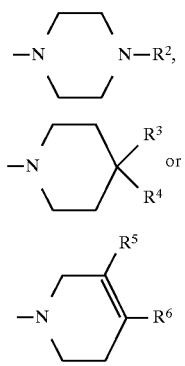

wherein

R² is hydrogen, alkyl of 1 to 6 carbon atoms, cycloalkyl of 3 to 8 carbon atoms, phenyl optionally substituted with R¹ as defined above; ω-phenylalkyl or ω-diphenylalkyl, in which the alkyl chain contains 1 to 4 carbon atoms and the phenyl ring is optionally substituted with R¹ as defined above, or R² is naphthyl, indolyl, indazolyl, thienyl, pyridinyl, pyrimidinyl, quinolinyl, benzoisothiazolyl or benzisoxazolyl, each optionally substituted with R¹ as defined above;

R³ is hydrogen and R⁴ is hydrogen, 1-benzimidazolyl-2-one, indolyl, benzoisothiazolyl or benzisoxazole, each optionally substituted with R¹ as defined above, or R⁴ is —Y—Ar, in which Y is C═O, CHOH, or $(CH_2)_m$, wherein m is 0 to 4, and Ar is phenyl, optionally substituted with R¹ as defined above, or R³ and R⁴, taken together with the carbon atom to which they are attached form

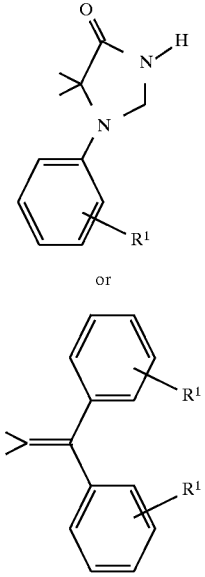

R⁵ is hydrogen and R⁶ is phenyl, naphthyl, thienyl, indolyl, benzoisothiazolyl or benzisoxazolyl, each optionally substituted with R¹ as defined above, or R⁵ and R⁶, taken together with the carbon atoms to which they are attached complete a benzene ring optionally substituted with R¹;

or a pharmaceutically acceptable salt thereof.

2. A compound of claim 1 in which R² is phenyl, naphthyl, indolyl, indazolyl, thienyl, pyridinyl, pyrimidinyl, quinolinyl, benzoisothiazolyl or benzisoxazolyl, each optionally substituted with R¹ as defined in claim 1, R³ is hydrogen and R⁴ is 1-benzimidazolyl-2-one, indolyl, benzoisothiazolyl or benzisoxazolyl, each optionally substituted with R¹ as defined in claim 1, or R⁴ is —Y—Ar, in which Y is C═O, and Ar is phenyl, optionally substituted with R¹ as defined in claim 1, R⁵ is hydrogen and R⁶ is phenyl, indolyl, benzoisothiazolyl or benzisoxazolyl, each optionally substituted with R¹ as defined in claim 1, or R⁵ and R⁶, taken together with the carbon atoms to which they are attached complete a benzene ring optionally substituted with R¹;

or a pharmaceutically acceptable salt thereof.

3. A compound of claim 1 in which X is $H_2$, R² is phenyl, indolyl, pyridinyl, pyrimidinyl, quinolinyl, benzoisothiazolyl or benzisoxazolyl, each optionally substituted with R¹ as defined in claim 1, R⁵ is hydrogen and R⁶ is phenyl, optionally substituted with R¹ as defined above, or R⁵ and R⁶, taken together with the carbon atoms to which they are attached complete a benzene ring optionally substituted with R¹; or a pharmaceutically acceptable salt thereof.

4. The compound of claim 1 which is 2-(3,4-dihydro-1H-isoquinolin-2-ylmethyl)-2,3,8,9-tetrahydro-7H-1,4-dioxino[2,3-e]indol-8-one or a pharmaceutically acceptable salt thereof.

5. The compound of claim 1 which is 2-[4-(4-fluoro-benzoyl)-piperidin-1-ylmethyl]-2,3,8,9-tetrahydro-7H-1,4-dioxino[2,3-e]indol-8-one or a pharmaceutically acceptable salt thereof.

6. The compound of claim 1 which is 2-(4-oxo-1-phenyl-1,3,8-triaza-spiro[4,5]dec-8-ylmethyl)-2,3,8,9-tetrahydro-7H-1,4-dioxino-[2,3-e]indol-8-one or a pharmaceutically acceptable salt thereof.

7. The compound of claim 1 which is 2-[4-(2-oxo-2,3-dihydro-benzimidazol-1-yl)-piperidin-1-ylmethyl]-2,3,8,9-tetrahydro-7H-1,4-dioxino[2,3-e]indol-8-one or a pharmaceutically acceptable salt thereof.

8. The compound of claim 1 which is 2-(4-phenyl-3,6-dihydro-2H-pyridin-1-ylmethyl)-2,3,8,9-tetrahydro-7H-1,4-dioxino[2,3-e]indol-8-one or a pharmaceutically acceptable salt thereof.

9. The compound of claim 1 which is 2-[4-(1H-indol-4-yl)-piperazin-1-ylmethyl]-2,3,8,9-tetrahydro-7H-1,4-dioxino[2,3-e]indol-8-one or a pharmaceutically acceptable salt thereof.

10. The compound of claim 1 which is 2-(3,4-dihydro-1H-isoquinolin-2-ylmethyl)-6-fluoro-2,3,8,9-tetrahydro-7H-1,4-dioxino[2,3-e]indol-8-one or a pharmaceutically acceptable salt thereof.

11. The compound of claim 1 which is 2-[4-(1H-indol-3-yl)-1-piperidinylmethyl]-6-fluoro-2,3,8,9-tetrahydro-7H-1,4-dioxino[2,3-e]indol-8-one or a pharmaceutically acceptable salt thereof.

12. The compound of claim 1 which is 2-[4-(1,2-benzisothiazol-3-yl)-1-piperazinylmethyl)-2,3,8,9-tetrahydro-7H-1,4-dioxino[2,3-e]indol-8-one or a pharmaceutically acceptable salt thereof.

13. The compound of claim 1 which is 2-[4-(6-fluoro-1,2-benzisoxazol-3-yl)-1-piperidinylmethyl]-2,3,8,9-tetrahydro-7H-1,4-dioxino[2,3-e]indol-8-one or a pharmaceutically acceptable salt thereof.

14. The compound of claim 1 which is 4-fluoro-8-[4-(1H-indol-3-yl)-3,6-dihydro-2H-pyridin-1 -ylmethyl]-1,3,7,8-tetrahydro-6,9-dioxa-3-aza-cyclopenta[a]naphthalen-2-one or a pharmaceutically acceptable salt thereof.

15. A method for treatment of diseases of brain dopamine dysregulation which comprises administering, orally or parenterally, to a subject suffering from such a disorder of the dopaminergic system, an amount of a compound of formula I

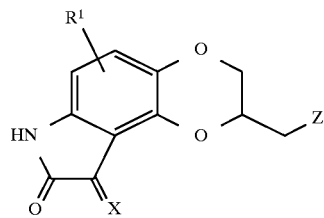

wherein

X is H$_2$ or O;

R$^1$ is hydrogen, hydroxy, halo, trifluoromethyl, trifluoromethoxy, alkyl of 1 to 6 carbon atoms, alkoxy of 1 to 6 carbon atoms, aralkoxy of 7 to 12 carbon atoms, alkanoyloxy of 2 to 6 carbon atoms, amino, mono- or di-alkylamino in which each alkyl group has 1 to 6 carbon atoms, alkanamido of 2 to 6 carbon atoms or alkanesulfonamido of 1 to 6 carbon atoms;

Z is

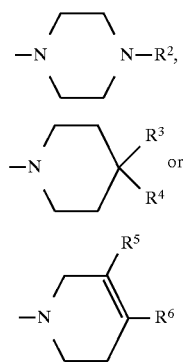

wherein

R$^2$ is hydrogen, alkyl of 1 to 6 carbon atoms, cycloalkyl of 3 to 8 carbon atoms, phenyl optionally substituted with R$^1$ as defined above; ω-phenylalkyl or ω-diphenylalkyl, in which the alkyl chain contains 1 to 4 carbon atoms and the phenyl is optionally substituted with R$^1$ as defined above, or R$^2$ is naphthyl, indolyl, indazolyl, thienyl, pyridinyl, pyriridinyl, quinolinyl, benzoisothiazolyl or benzisoxazolyl, each optionally substituted with R$^1$ as defined above;

R$^3$ is hydrogen and R$^4$ is hydrogen, 1-benzimidazolyl-2-one, indolyl, benzoisothiazolyl or benzisoxazolyl, each optionally substituted with R$^1$ as defined above, or R$^4$ is —Y—Ar, in which Y is C=O, CHOH, or (CH$_2$)$_m$, wherein m is 0 to 4, and Ar is phenyl, optionally substituted with R$^1$ as defined above, or R$^3$ and R$^4$, taken together with the carbon atom to which they are attached form

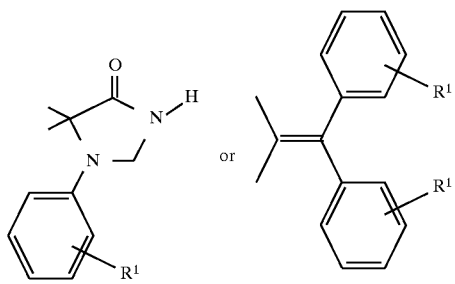

R$^5$ is hydrogen and R$^6$ is phenyl, naphthyl, thienyl, indolyl, benzoisothiazolyl or benzisoxazolyl, each optionally substituted with R$^1$ as defined above, or R$^5$ and R$^6$, taken together with the carbon atoms to which they are attached complete a benzene ring optionally substituted with R$^1$;

or a pharmaceutically acceptable salt thereof;

sufficient to alleviate the symptoms of said brain dopamine dysregulation.

16. A method of claim 15, for treatment of schizophrenia or a schizoaffective disorder, which comprises administering, orally or parenterally, to a subject suffering from dysregulation of the dopaminergic system, an amount of a compound of formula I:

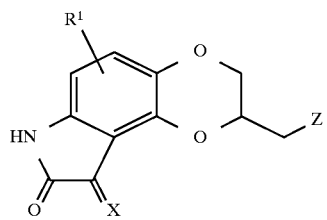

wherein

X is H$_2$ or O;

R$^1$ is hydrogen, hydroxy, halo, trifluoromethyl, trifluoromethoxy, alkyl of 1 to 6 carbon atoms, alkoxy of 1 to 6 carbon atoms, aralkoxy of 7 to 12 carbon atoms, alkanoyloxy of 2 to 6 carbon atoms, amino, mono- or di-alkylamino in which each alkyl group has 1 to 6 carbon atoms, alkanamido of 2 to 6 carbon atoms or alkanesulfonamido of 1 to 6 carbon atoms;

Z is

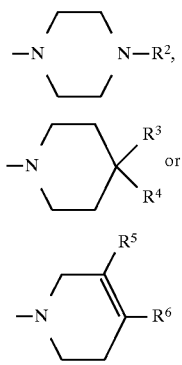

wherein

R$^2$ is hydrogen, alkyl of 1 to 6 carbon atoms, cycloalkyl of 3 to 8 carbon atoms, phenyl optionally substituted with R$^1$ as defined above; ω-phenylalkyl or ω-diphenylalkyl, in which the alkyl chain contains 1 to 4 carbon atoms and the phenyl is optionally substituted with $R^1$ as defined above, or $R^2$ is naphthyl, indolyl, indazolyl, thienyl, pyridinyl, pyrimidinyl, quinolinyl, benzoisothiazolyl or benzisoxazolyl, each optionally substituted with $R^1$ as defined above;

$R^3$ is hydrogen and $R^4$ is hydrogen, 1-benzimidazolyl-2-one, indolyl, benzoisothiazolyl or benzisoxazolyl, each optionally substituted with $R^1$ as defined above, or $R^4$ is —Y—Ar, in which Y is C=O, CHOH, or $(CH_2)_m$, wherein m is 0 to 4, and Ar is phenyl, optionally substituted with $R^1$ as defined above, or $R^3$ and $R^4$, taken together with the carbon atom to which they are attached form

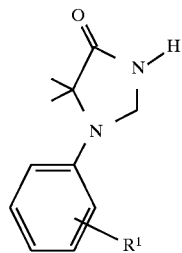

or

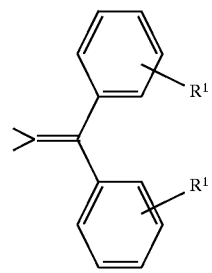

$R^5$ is hydrogen and $R^6$ is phenyl, naphthyl, thienyl, indolyl, benzoisothiazolyl or benzisoxazolyl, each optionally substituted with $R^1$ as defined above, or $R^5$ and $R^6$, taken together with the carbon atoms to which they are attached complete a benzene ring optionally substituted with $R^1$;

or a pharmaceutically acceptable salt thereof;

sufficient to alleviate the symptoms of said schizophrenia or schizoaffective disorder.

* * * * *